United States Patent [19]

Guieze et al.

[11] Patent Number: 4,864,843
[45] Date of Patent: Sep. 12, 1989

[54] METHOD AND APPARATUS FOR CHROMATOGRAPHIC ANALYSIS, IN PARTICULAR OF PETROLEUM LIQUIDS

[75] Inventors: Paul B. Guieze, Nangis; Nikos Varotsis, Avon, both of France

[73] Assignee: Schlumberger Technology Corporation, Houston, Tex.

[21] Appl. No.: 267,641

[22] Filed: Nov. 3, 1988

Related U.S. Application Data

[63] Continuation of Ser. No. 51,809, May 18, 1987, abandoned.

[30] Foreign Application Priority Data

May 22, 1986 [FR] France ................................ 86 07323

[51] Int. Cl.⁴ ............................................. G01N 31/08
[52] U.S. Cl. ....................................... 73/23.1; 422/89
[58] Field of Search ......................... 73/23.1; 436/161; 422/89

[56] References Cited

U.S. PATENT DOCUMENTS

| | | | |
|---|---|---|---|
| 3,030,798 | 4/1962 | Lichtenfels | 73/23.1 |
| 3,169,389 | 2/1965 | Green, Jr. et al. | 73/23.1 |
| 3,444,722 | 5/1969 | Roof | 73/23.1 |
| 3,607,075 | 9/1971 | Wolf | 73/23.1 |
| 4,035,168 | 7/1977 | Jennings | 73/23.1 |
| 4,287,752 | 9/1981 | Ury | 73/23.1 |

FOREIGN PATENT DOCUMENTS

51778  5/1982  European Pat. Off. ............. 422/89

OTHER PUBLICATIONS

McCoy et al; On-Line Stream Analysis with a Chromatograph; Control Engineering, vol. 17, No. 7 (Jul. 1970).

Primary Examiner—Hezron E. Williams
Attorney, Agent, or Firm—Henry N. Garrana; John H. Bouchard

[57] ABSTRACT

A liquid sample to be analyzed is subjected to a vaporizing step. The vaporized components are submitted to a first separation stage by introducing said components into a packed chromatography column and flowing carrier gas through said column. The effluent of the first stage is passed through a flow dividing chamber. A second separation stage is performed by passing the effluent of the flow dividing chamber to a capillary chromatography column and flowing carrier gas therethrough. After a predetermined period of time, flushing gas is introduced through the flow dividing chamber and flowed through the first-stage packed column in a direction opposite to the original direction of flow while the direction of flow remains unchanged in the capillary column.

9 Claims, 3 Drawing Sheets

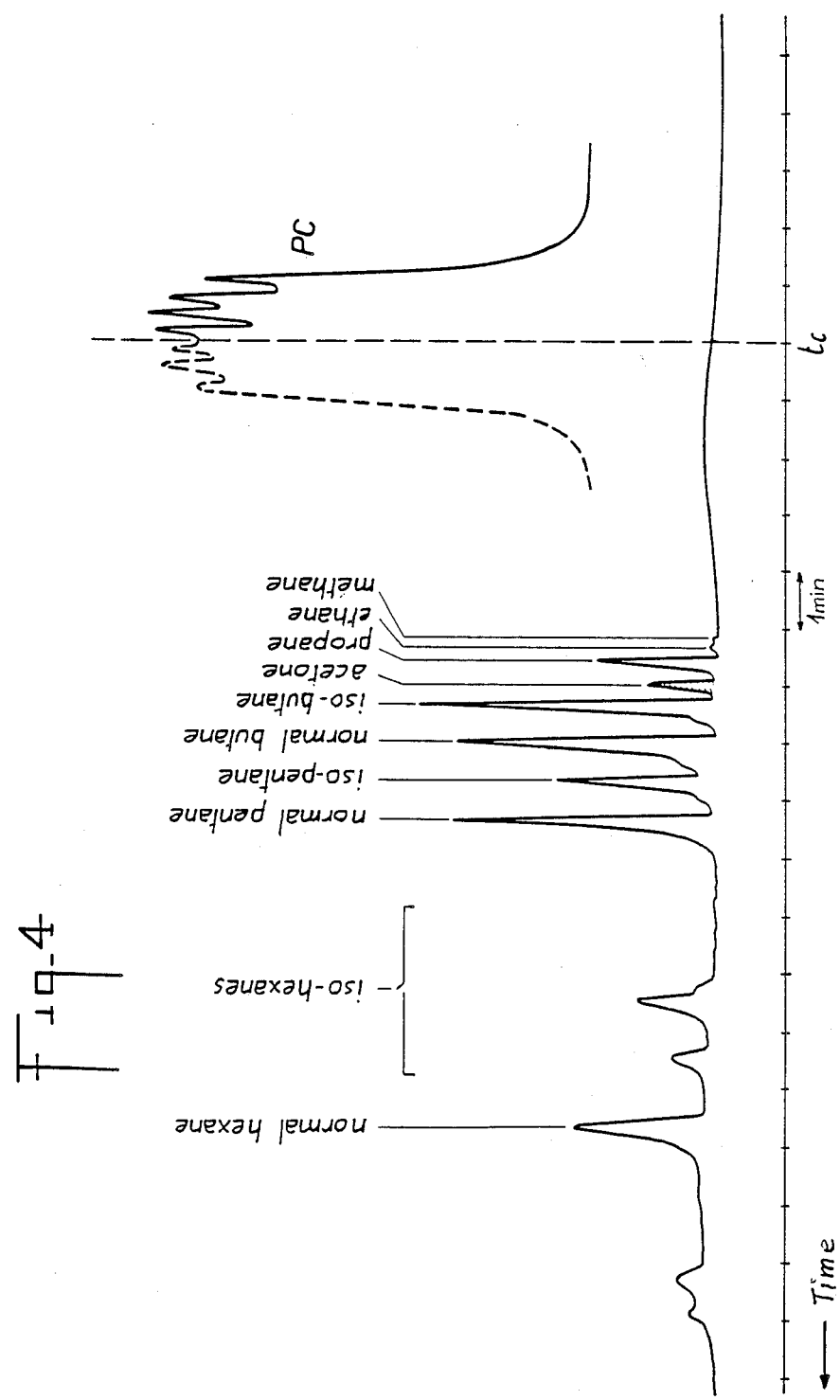

METHOD AND APPARATUS FOR CHROMATOGRAPHIC ANALYSIS, IN PARTICULAR OF PETROLEUM LIQUIDS

This is a continuation of application Ser. No. 051,809, now abandoned filed May 18, 1987.

The present invention relates to a method of analysis by gas chromatography, in which a liquid substance to be analyzed, more particularly a crude petroleum oil, is put into gaseous form, and is conveyed by means of a carrier gas along an analysis column system for chromatographic separation, and the ligher components of said substance are detected as they leave said column system in succession. The invention also relates to an apparatus for carrying out such method.

BACKGROUND OF THE INVENTION

Heretofore, petroleum liquids have generally been analyzed in the laboratory, or on site in a laboratory cabin which reproduces laboratory conditions. The liquid is initially separated into a light portion and a heavy portion by means of a distillation apparatus. The light portion is analyzed by means of a gas chromatograph, whereas only two or three overall physical measurements are used to characterize the heavy portion (e.g. molar mass, density, . . . ). This method suffers from the drawback of requiring additional apparatus (for distillation) which is difficult and lengthy to put into operation. Further, the operations of recovering and measuring the various products may give rise to additional sources of error. In some laboratories, the liquid is injected directly into a gas chromatograph whose circuit comprises an injector, a short duct, and an analysis column. Quantitative analysis is performed by means of the method using an internal standard. This method makes it possible to avoid prior separation, but the system becomes polluted very quickly if heavy oils are injected therein, since the intermediate components migrate slowly but irremediably along the short duct and thus reach the analysis column.

In order to overcome this drawback, it has been proposed in U.S. Pat. No 3,030,798 to Lichtenfels a two-stage process using two packed columns connected in series. In this known technique, the fluid mixture to be analyzed is initially injected into the first column and carrier gas is flowed through the first and the second column. When all the components of interest i.e. the lighter components have emerged from the first column, the direction of flow of the carrier gas in the first column is reversed while it remains unchanged in the second column. The effect is to remove from the first column the heavier components which remain therein, and once this backflushing is completed, the first column is in condition for receiving another charge to be analyzed. At the same time, the analysis continues in the second column.

The system described in this patent is disadvantageous in that the flow of carrier gas is controlled by valves which are part of the circuit through which the substance to be analyzed is circulated. This may give rise to leaks and creates "lost volumes" detrimental to the accuracy of the analysis.

The aim of the present invention is to make it possible to analyze the components of a sample of crude oil stored under atmospheric conditions. This analysis should be capable of being performed on a drilling site using portable equipment and without taking special precautions, and it should be possible to analyze a large number of samples in succession without the need for any maintenance operation. High accuracy should be achieved concerning the lighter portion of the liquid (up to $C_6$ components). No restriction should exist with regard to the type of crude oil capable of being analyzed.

SUMMARY OF THE INVENTION

In accordance with the present invention, a sample of the crude oil to be analyzed is subjected to a vaporizing step. The vaporized components are submitted to a first separation stage by introducing said components into a packed chromatography column and flowing carrier gas through said column. The effluent of the first stage is passed through a flow dividing chamber. A second separation stage is performed by passing the effluent of the flow dividing chamber to a capillary chromatography column and flowing carrier gas therethrough. After a predetermined period of time, flushing gas is introduced through the flow dividing chamber and flowed through the first-stage packed column in a direction opposite to the original direction of flow while the direction of flow remains unchanged in the capillary column.

Advantageously, the components separated as a result of the first separation stage and leaving the first-stage column in succession are mixed in the flow dividing chamber, whereby they arrive together at the inlet of the second-stage capillary column.

BRIEF DESCRIPTION OF THE DRAWINGS

An implementation of the invention is described by way of example with reference to the accompanying drawings, in which:

FIG. 4 is an example of a chromatogram obtained during analysis of a petroleum substance.

MORE DETAILED DESCRIPTION

Figure 1:
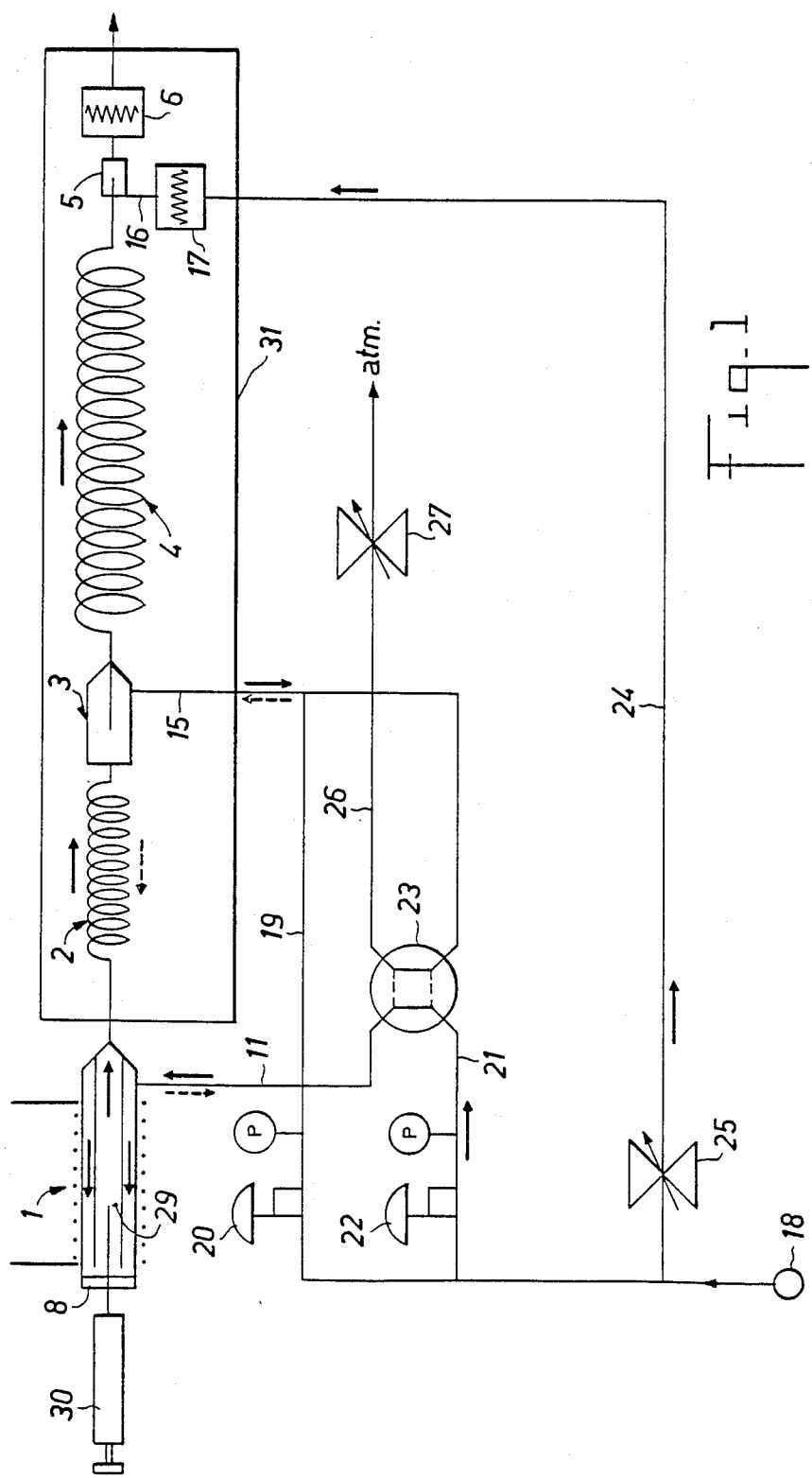
FIG. 1 is a diagram showing the structure of a chromatographic apparatus in accordance with the invention.

The apparatus shown diagrammatically in FIG. 1 comprises an analysis circuit, or main circuit, along which at least some of the components of the substance to be analyzed are made to flow, and an auxiliary circuit for the carrier gas which is used to transport the components of said substance in gaseous form. The main circuit comprises an injector 1, a first chromatographic column 2, referred to below as the pre-column, an intermediate chamber 3, a second chromatograhic column 4, referred to below as the analysis column, a device 5 for adding carrier gas, and an analysis detector 6, with all of said items being connected in series.

Figure 2:
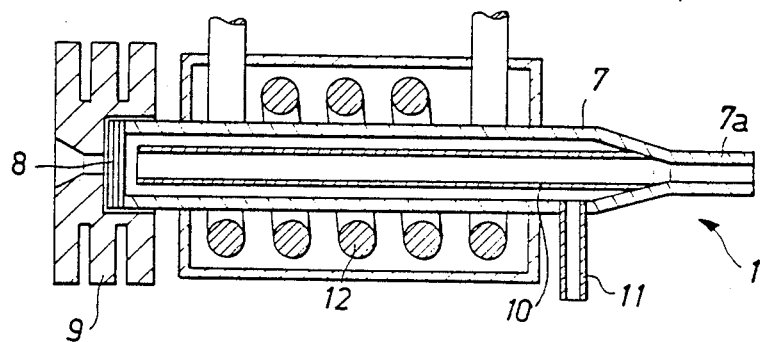
FIGS. 2 and 3 are longitudinal sections on a larger scale respectively through the injector and through the intermediate chamber of the FIG. 1 apparatus.

The injector 1 (see FIG. 2) is intended to vaporize the components of the substance to be analyzed and to inject them into the pre-column 2. It comprises an elongate enclosure 7 which extends horizontally and is closed at one end by a septum 8 (i.e. a disk of resilient material capable of being pierced by a needle). The septum is held in place by a cap 9. The other end 7a of the enclosure 7 is connected to the inlet of the pre-column 2. A removable tube 10 of borosilicate glass is disposed horizontally inside the enclosure having one end connected in sealed manner to the outlet end 7a of the enclosure 7 and having its other end stopping short of the septum 8, thereby putting both portions of the inside volume of the enclosure 7 as separated by the tube 10 into communication with each other at said end. A duct 11 is connected to the enclosure 7 close to its end 7a for injecting a carrier gas for transporting the fluid to be analyzed towards said main circuit. The enclosure 7 is surrounded by heater elements 12 for raising it to a high enough temperature to vaporize the components of the substance to be analyzed as inserted into the injector.

The pre-column 2 is a packed chromatographic column containing an inert support impregnated with a liquid for cooperating with the gaseous components to be separated. The purpose of the pre-column 2 is to separate the lighter components of the fluid to be analyzed from the heavier portion vaporized in the injector 1, but which is not wanted for analysis purposes.

Figure 3:
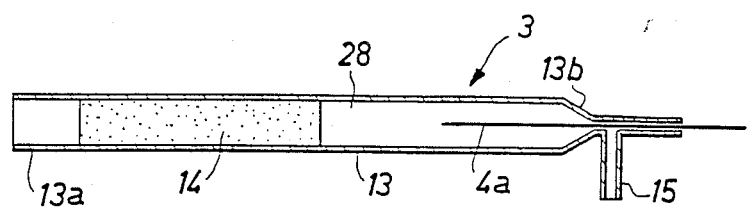

The intermediate chamber 3 is constituted (see FIG. 3) by a tube 13 containing a porous body 14 such as a plug of quartz wool extending over a portion of its length adjacent to its end 13a by which it is connected to the pre-column 2. The inlet end 4a of the analysis column 4 penetrates into the tube 13 via the opposite end 13b thereof in order to sample the gaseous fluid in the central region of the non-turbulent zone 28 left free inside the tube 13 by the porous body 14. A duct 15 is also connected to said end of the tube 13 in order to remove a portion of the gaseous fluid coming from the precolumn 2. The first function of the chamber 3 is to divide the gas flow which it recieves from the pre-column 2 into two portions and to apply a gas flow to the analysis column 4 which is compatible with the capabilities thereof, with the remainder of the flow being exhausted to the atmosphere via the duct 15.

The analysis column 4 is a very long capillary tube of the "open tube" type which serves to separate the components selected by the pre-column 2 for analysis purposes, with analysis being performed by means of the detector 6 which is constituted by a thermal conductivity cell or "katharometer". In order to ensure that the conductivity cell operates under good conditions, in spite of the very low flow rate along the capillary column 4, the column opens out into a mixing chamber belonging to the device 5 for adding in a flow of carrier gas received via a duct 16, with said duct 16 including a reference detector 17 similar to the analysis detector 6. The columns 2 and 4, the intermediate chamber 3, the carrier gas adding device 5, and the detectors 6 and 17 are all placed in a constant temperature enclosure 31, which may be a simple oven which is isothermally regulated by inertia.

The auxiliary circuit is a pneumatic circuit comprising an inlet for the carrier gas 18 suitable for connection to a cylinder of compressed gas (e.g. helium). This inlet 18 is connected via a duct 19 including a pressure regulated 20 to the duct 15 which is connected to the division chamber 3, and via a duct 21 fitted with a flow rate regulator 22 and a four-path valve 23 to the duct 11 which is connected to the injector 1 and via a duct 24 including a micrometer valve 25 for adjusting a flow rate limit to the device 5 for adding carrier gas via the detector 17 and the duct 16. The duct 15 of the division chamber 3 is connected not only to the duct 19 but also via the four path valve 23 to a duct 26 leading to the atmosphere via an adjustable flow rate limiting valve 27.

The above-described connections between the ducts 11, 21, 15, and 16 connected to the valve 23 correspond to the position shown of its moving switch member, which position interconnects 11 to 21 and 15 to 26 as shown by solid lines. When this switch element is rotated through 90°, it then interconnects 15 to 21 and 11 to 26, as indicated by dashed lines.

It is to be pointed out that the path through the elements 1, 2, 3, 4, 5, and 6 as followed by the substance to be analyzed, in other words the analysis circuit, does not include any switching valves.

The operation of the apparatus and the procedures for using it are described below.

A drop 29 of substance to be analyzed is inserted into the glass tube of the injector 1 by passing a syringe 30 through the septum 8 which is pierced by the needle of the syringe. This substance is a crude oil, i.e. a liquid mixture of hydrocarbons $C_nH_m$. The lightest components of this mixture are to be analyzed, which typically means components with $1<n<7$. If the substance is too thick in consistency, it may be dissolved in a diluent chosen in such a way as to avoid disturbing the results of the chromatographic analysis.

The heater element 12 of the injector 1 sets up a temperature therein such that all of the analytically interesting components of the mixture are vaporzied (the heaviest components may remain in the tube 10 in liquid form, thus separating them out early). The valve 23 is put in a position where it sets up the connections shown in solid lines and causes carrier gas to flow through the injector 1, the pre-column 2, and the intermediate chamber 3 in the direction indicated by solid arrows. This flow of gas coming from the inlet 18 thus passes at a constant flow rate fixed by the flow rate regulator 22 along the ducts 21 and 11, the tube 10 and the injector 1, the pre-column 2, the chamber 3, and the ducts 15 and 26 prior to escaping to the atmosphere via the adjustable outlet valve 27. Suitable adjustment of the outlet valve 27 raises the pressure in the chamber 3 to a value which is higher than atmospheric pressure and which is stabilized by the pressure regulator 20.

The flow of carrier gas set up in this way causes the vaporized components of the substance to be analyzed to circulate along the pre-column 2. The pre-column 2 provides coarse preliminary separation as shown by the diagrammatic curve PC in FIG. 4. This curve gives an idea of what would be obtained from an analysis detector (such as the detector 6) placed at the outlet from the pre-column 2. This initial separation serves to ensure that only those light components which are to be analyzed are, in fact, admitted into the analysis column 4 (the right-hand portion of the curve PC drawn in solid lines), while the remaining, heavier components are not admitted thereto (left-hand portion of the curve PC drawn in dashed lines). Said light components are mixed together again on arriving in the chamber 3 by the porous stopper 14 which they must pass through, and by the volume given to said chamber which is selected to be relatively large with regard to the gaseous volume of the vaporized portion of the initial substance. All of these components thus arrive simultaneously at the inlet 4a of the analysis column 4 and enter said column together. At an instant $t_c$ (as experimentally determined during earlier tests), all of the interesting components in the range $C_1$ to $C_n$ (and preferably including one or two of the next components, by way of precaution) have entered the analysis column 4 and are also to be found in the chamber 3, whereas the heavier components which are not to be analyzed individually and which correspond to the left-hand portion of the curve PC, still remain in the chamber 3 or have not yet left the pre-column 2.

At this moment, the switching valve is operated to set up the connections shown in dashed lines. As a result the flow direction of the carrier gas through the pre-column is reversed, thereby backwashing said heavier components from the pre-column into the injector 1 from which they are finally rejected to the atmosphere via the ducts 11 and 26 and via the valve 27. This reversal of the gas flow direction serves firstly to avoid polluting the column 4 with the unwanted portion of the sample, and secondly to backwash not only the pre-column 2, but also the chamber 3 and the injector 1, thereby cleaning them thoroughly so that said items do not accumulate unwanted matter and can therefore be used many times over without requiring any other form of cleaning, or replacement. In particular, the residue of non-vaporized heavy components from each sample inserted into the injector is relieved of its lighter components which are not wanted for analysis purposes and can therefore remain in the injector during following analyses, thereby reducing the frequency with which the sample-receiving glass tube 10 needs to be replaced.

During the initial operating period prior to the switch-over instant $t_c$, only a fraction of the gas flow leaving the pre-column 2 is admitted into the column 4, by virtue of the division effect provided by the chamber 3, with the excess portion of said gas mixture (components to be analyzed plus carrier gas) being rejected to the atmosphere via the ducts 15 and 26 and the adjustable valve 27. The division ratio corresponds to the ratio of the operating flow rates of the two columns 2 and 4, with the operating flow rate of the column 4 (which is a capillary column) being very much less than that of the pre-column 2.

The light components admitted into the analysis column 4 flow therealong while being subjected to fine chromatographic separation as shown up by the detector 6 in the form of a chart similar to that shown in FIG. 4, which corresponds to an analysis of the $C_6$- components of a crude petroleum oil. An internal reference (a known quantity of acetone) is added to the sample inserted into the apparatus and produces a (shaded) peak between two peaks of sample components, thereby making quantitative analysis of the sample possible.

Highly viscous samples may be diluted in a solvent in order to facilitate taking samples using the chromatographic syringe 30. The solvent should be chosen so that the time it requires for being eluted along the pre-column 2 is greater than the time required for the slowest component of interest, so that the solvent remains in the portion which is not admitted into the analysis column 4, and which therefore does not appear on the chromatogram.

It should be observed that the operating regime of the column 4 is absolutely uniform and stable throughout both operating stages (as distinguished by switching over the valve 23) since the pressure applied to the inlet 4a of said column (i.e. the pressure in the chamber 3) is kept permanently constant by the pressure regulator 20 whose output is connected via the ducts 19 and 15 to said chamber. For example, an apparatus in accordance with the invention for performing chromatographic analysis of petroleum products (samples of crude oil) may have it main component parts selected to have the following dimensions and characteristics.

Pre-column 2: a stainless steel column which is about 1.5 meters (m) long, having a diameter of about 3 mm, filled with "Chromosorb PAW" medium (having a granulometry of 80 to 100 mesh, i.e. about 0.18 to about 0.15 mm), impregnated with 15% "SE30" silicon to constitute the stationary liquid phase, and operating at a flow rate of about 20 to 40 $cm^3$/min. It is capable of receiving an inlet gas sample having a volume of about 1 $cm^3$ (5 $mm^3$ in the liquid state), mixed with the vector glass flow.

Intermediate chamber 3: tubular chamber 45 mm long with a diameter of 4 mm containing a 20 mm long quartz wool plug 14 in its half closest to its inlet connected to the pre-column 2, with the distance between the inlet end 4a to the column 4, and the adjacent end face of the plug 14 being 10 mm. The inside volume of such a chamber is suitable for the pre-column having a volume of substance injected thereto corresponding to 1 $cm^3$ of gas or 5 $mm^3$ of liquid.

Analysis column 4: a stainless steel capillary column having a length of 100 m, a bore whose inside diameter is equal to 0.25 mm and is lined with a 0.2 $\mu$m thick film of "Squalane" constituting the stationary liquid phase, and operating a flow rate of about 0.8 to 1.5 $cm^3$/min. (i.e. about one-thirtieth of the flow rate applicable to the pre-column).

We claim:

1. A method of analyzing by gas chromatography the components of a sample or crude oil, comprising the steps of:
    vaporizing said sample thereby producing vaporized components;
    introducing the vaporized components of said sample into a first packed column of a first separation stage;
    flowing first carrier gas into saisd first packed column of said first separation stage, the first packed column producing effluent;
    passing the effluent and the first carrier gas from the first packed column into a flow dividing chamber;
    in said flow dividing chamber, mixing together said effluent and said first carrier gas to produce a gas mixture and dividing the gas mixture into a first portion and a second portion;
    passing said first portion of said gas mixture from said flow dividing chamber into a second capillary column;
    discharging said second portion of said gas mixture to a surrounding atmosphere;
    performing a second separation stage of said first portion of said gas mixture in said second capillary column; and
    subsequently, introducing a second carrier gas into said flow dividing chamber and flowing said second carrier gas in a first direction, through said first packed column, which is opposite to the direction of flow of said first carrier gas and in a second direction, through said second capillary column, which is the same as the direction of flow of said first carrier gas.

2. The method of claim 1, wherein a temperature in the first and second separation stages is maintained at a constant value, a temperature during the vaporizing step being higher than said constant value.

3. The method of claim 1, wherein a flow rate in said first packed column is maintained constant, a pressure at an inlet of siad second capillary column being maintained constant.

4. An apparatus for analyzing by gas chromatography the components of a sample of crude oil, comprising:
- a packed chromatography column;
- a capillary chromatography column;
- a flow dividing chamber connected between the outlet of said packed column and the inlet of said capillary column;
- means for vaporizing said sample;
- means for introducing the vaporized components into said packed column;
- means for establishing a flow of carrier gas in a first direction to cause said components to circulate, at a constant flow rate, through said packed column, through said flow dividing chamber, and through said capillary column at a constant pressure;
- means connected to said flow dividing chamber for discharging a portion of said carrier gas, in said flow dividing chamber, to an atmosphere during the establishment of said flow of carrier gas in said first direction through said flow dividing chamber by said means for establishing; and
- valve means for terminating the flow of carrier gas through said packed column in said first direction and for introducing carrier gas into the flow dividing chamber to establish a flow of carrier gas in said packed column in a second direction which is opposite to said first direction.

5. The apparatus of claim 4, wherein said flow dividing chamber includes means for mixing together the vaporized components as they are separated at the outlet of said packed column.

6. The apparatus of claim 4, comprising a flow rate regulator for maintaining at a constant value the flow rate of carrier gas flowing through the packed column, and a pressure regulator for maintaining at a constant value the pressure of carrier gas at the inlet of the capillary column.

7. The apparatus of claim 4, comprising a thermostatic enclosure inside which the columns and the flow dividing chamber are received, said vaporizing means being located outside said enclosure.

8. The apparatus of claim 4, further comprising mixing chamber means connected to an output of said capillary column and to the means for establishing for receiving said carrier gas from the means for establishing and mixing said carrier gas with an effluent output from said capillary column thereby producing a gas mixture.

9. The apparatus of claim 8, further comprising analysis detector means connected to said mixing chamber means for analyzing said gas mixture output from said mixing chamber means.

* * * * *